US011864907B2

(12) United States Patent
Duval et al.

(10) Patent No.: US 11,864,907 B2
(45) Date of Patent: Jan. 9, 2024

(54) DEVICES, SYSTEMS, AND METHODS FOR MONITORING GASTROINTESTINAL MOTILITY

(71) Applicant: Boston Scientific Scimed, Inc., Maple Grove, MN (US)

(72) Inventors: George Wilfred Duval, Sudbury, MA (US); Bryan Allen Clark, Forest Lake, MN (US); John Allen Hingston, Framingham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1266 days.

(21) Appl. No.: 16/247,716

(22) Filed: Jan. 15, 2019

(65) Prior Publication Data
US 2019/0216384 A1 Jul. 18, 2019

Related U.S. Application Data

(60) Provisional application No. 62/617,877, filed on Jan. 16, 2018.

(51) Int. Cl.
*A61B 5/00* (2006.01)
*A61B 7/00* (2006.01)
*A61B 5/07* (2006.01)

(52) U.S. Cl.
CPC .............. *A61B 5/42* (2013.01); *A61B 5/7264* (2013.01); *A61B 7/008* (2013.01); *A61B 5/073* (2013.01); *A61B 5/7257* (2013.01); *A61B 5/7275* (2013.01); *A61B 2562/0219* (2013.01)

(58) Field of Classification Search
CPC .......... A61B 5/42; A61B 5/073; A61B 5/7264
See application file for complete search history.

(56) References Cited

U.S. PATENT DOCUMENTS

| 5,690,691 | A | 11/1997 | Chen et al. |
| 6,374,670 | B1 | 4/2002 | Spelman et al. |
| 6,754,536 | B2 | 6/2004 | Swoyer et al. |
| 7,338,444 | B2 | 3/2008 | Ben-Oren et al. |
| 7,693,577 | B2 | 4/2010 | Knudson et al. |
| 9,161,703 | B2 | 10/2015 | Wu et al. |
| 9,474,482 | B2 | 10/2016 | Devanaboyina |
| 9,486,154 | B2 | 11/2016 | Fu |
| 2004/0143182 | A1 | 7/2004 | Kucera et al. |

(Continued)

FOREIGN PATENT DOCUMENTS

WO 2012/060874 A2 5/2012

OTHER PUBLICATIONS

Charles N. Bernstein et al., "A Prospective Population-Based Study of Triggers of Symptomatic Flares in IBD", The Americal Journal of Gastroenterology, vol. 105, Sep. 2010 (9 pages).

(Continued)

*Primary Examiner* — Puya Agahi
(74) *Attorney, Agent, or Firm* — Bookoff McAndrews, PLLC (57) ABSTRACT

A method for evaluating a gastrointestinal tract may include receiving an electrical signal that includes data pertaining to motility in the gastrointestinal tract of a patient and analyzing one or more characteristics of the electrical signal relative to one or more respective thresholds indicative of an occurrence or an imminence of a condition of the gastrointestinal tract.

20 Claims, 4 Drawing Sheets

(56) References Cited

U.S. PATENT DOCUMENTS

| | | | |
|---|---|---|---|
| 2008/0262313 A1* | 10/2008 | Shimizu | A61B 5/42 600/160 |
| 2008/0306348 A1 | 12/2008 | Kuo et al. | |
| 2008/0306355 A1 | 12/2008 | Walker | |
| 2011/0040203 A1 | 2/2011 | Savage et al. | |
| 2014/0058282 A1* | 2/2014 | O'Grady | A61B 5/42 600/546 |
| 2014/0128688 A1 | 5/2014 | Wu et al. | |
| 2015/0366504 A1 | 12/2015 | Connor | |
| 2016/0045137 A1 | 2/2016 | Axelrod | |

OTHER PUBLICATIONS

Fotis Barkas et al., "Electrolyte and acid-base disorders in inflammatory bowel disease", Annals of Gastroenterology, 2013, vol. 26, Issue 1, pp. 23-28 (6 pages).

Shu Zhao et al., "Electrical bioimpedance gastric motility measurement based on an electrical-mechanical composite mechanism", World Journal of Gastroenterology, Jul. 7, 2012, vol. 18, Issue 25, pp. 3282-3287 (6 pages).

P Ducrotte et al., "Jejunal motility during cyclic total parenteral nutrition in patients with Crohn's disease", Gut, 1989, vol. 30, pp. 815-819 (5 pages).

Gabrio Bassotti et al., "Gastrointestinal motility disorders in inflammatory bowel diseases", World Journey of Gastroenterology, Jan. 7, 2014, vol. 20, Issue 1, pp. 37-44 (9 pages).

Jieyun Yin et al., "Electrography: Methodology, Validation and Applications", Journal of Neurogastroenterology and Motility, vol. 19, No. 1, Jan. 2013, pp. 5-17 (13 pages).

Foram Mehta, "Report: Economic Implications of Inflammatory Bowel Disease and Its Management", American Journal of Managed Care, Mar. 2016, vol. 22, No. 3, pp. S51-S60 (10 pages).

Global Inflammatory Bowel Disease Market 2015-2019, Jul. 29, 2015, https://www.prnewswire.com/news-releases/global-inflammatory-bowel-disease-market-2015-2019-300118433.htm.

* cited by examiner

DEVICES, SYSTEMS, AND METHODS FOR MONITORING GASTROINTESTINAL MOTILITY

CROSS-REFERENCE TO RELATED APPLICATIONS

This application claims the benefit of priority from U.S. Provisional Application No. 62/617,877, filed on Jan. 16, 2018, which is incorporated by reference herein in its entirety.

TECHNICAL FIELD

The present disclosure relates generally to devices, systems, and/or methods for monitoring gastrointestinal motility. More specifically, the present disclosure pertains to devices, systems, and/or methods for measuring and predicting motility using sensors.

BACKGROUND

Inflammatory Bowel Disease ("IBD") is a chronic disorder characterized by chronic inflammation in the gastrointestinal ("GI") tract. The disease affects 5-6 million people worldwide, with approximately 1.6 million sufferers in the United States. Patients and health care providers may spend substantial amounts of money per year treating IBD, with annual direct costs estimated between $11-28 billion in the United States. Moreover, people with IBD may have longer and more expensive hospitalizations with higher readmission rates than people without IBD.

There are two main types of IBD: Ulcerative Colitis ("UC") and Crohn's Disease ("CD"). CD can affect any part of the digestive system, and is characterized with transmural involvement. Symptoms of CD include abdominal pain, fever, cramping, rectal bleeding, and frequent diarrhea. The peak age for CD disease onset is between 15-35 years. UC affects the colon only, with mucosal involvement. UC carries mild to severe symptoms, which are similar to the symptoms of CD. With UC, complications may be less frequent than with CD. Colectomy may be used to treat UC. The peak age of disease onset for UC is between 15-30 and 50-70 years old. 55% of IBD patients have UC, and 45% of IBD patients have CD.

IBD is characterized by bouts of disease (also known as flare-ups). A correlation has been shown between inflammatory markers and gut motility disorders. For example, it has been reported that CD subjects have lower amplitudes for small bowel contractions with an increase of peristalsis frequency. Motor abnormalities have been shown to be more frequent in patients with active CD. Patients with inactive CD have also shown marked gastrointestinal motor disorders characterized by reduced incident of small bowel contractions and increased incidence of single or clustered propagated contractions.

To manage IBD, early diagnosis and treatment to prevent progression may be key. It may be particularly helpful to predict IBD flare-ups. Predictive and non-predictive IBD monitoring can potentially slow and/or prevent disease progression and/or allow patients to plan for upcoming flare-ups. Monitoring could also allow tailoring of IBD treatment using particular pharmaceutical agents or lifestyle changes. However, current treatments focus on addressing present symptoms and lack predictive ability. Despite studies to determine biomarkers of IBD, and despite discoveries regarding clinical variables, serological markers, fecal markers, and genetic tests, no single test is predictive and no monitoring system exists. Therefore, a need exists for systems and methods for predictive and non-predictive monitoring of IBD.

SUMMARY

Examples of the present disclosure relate to, among other things, devices, systems, and methods that may use sensors to monitor gastrointestinal motility. Each of the examples disclosed herein may include one or more of the features described in connection with any of the other disclosed examples.

In one example, a method for evaluating a gastrointestinal tract may comprise receiving an electrical signal that includes data pertaining to motility in the gastrointestinal tract of a patient; and analyzing one or more characteristics of the electrical signal relative to one or more respective thresholds indicative of an occurrence or an imminence of a condition of the gastrointestinal tract.

Any of the methods described herein may include one or more of the following features or steps: the one or more characteristics of the electrical signal may include at least one of a frequency, an amplitude, a measure of roughness, a fractal dimension, a minimum, a maximum, a segment endpoint, a short-time Fourier transform, or a discrete time Fourier transform; the analyzing step may include comparing a fractal dimension of the electrical signal to a first threshold value and if the fractal dimension is below the first threshold value, comparing an amplitude of the electrical signal to a second threshold value; the analyzing step may include evaluating whether an obstruction or a partial obstruction is occurring or imminent if the amplitude of the electrical signal is below the second threshold value, calculating one or more of a short-time Fourier transform or a discrete time Fourier transform of the electrical signal, and analyzing the one or more of the short-time Fourier transform or the discrete time Fourier transform for a change in frequency of the electrical signal; the method may include classifying the electrical signal as indicative of an occurrence or imminence of an obstruction or a partial obstruction if the change is to a lower frequency, or as indicative of a cluster event or an imminent cluster event if the change is to a higher frequency; the analyzing step may include classifying the electrical signal as indicative of a resting period or a fasting period if a fractal dimension of the electrical signal is lower than a threshold value; the condition of the gastrointestinal tract may be at least one of an obstruction, a partial obstruction, a flare-up of an inflammatory bowel disease, a resting period, a fasting period, or a cluster event; analyzing trends in the one or more characteristics of the electrical signal; the electrical signal may be generated by at least one sensor located within the patient's body; or the method may include at least one of generating an alert or administering a treatment, based on the occurrence or the imminence of the condition of the gastrointestinal tract.

In another example, a method for evaluating a gastrointestinal tract may include receiving an electrical signal that includes data pertaining to motility of the gastrointestinal tract over a first time period and a second time period; analyzing one or more characteristics of the electrical signal from the first time period relative to the second time period; and characterizing an occurrence or an imminence of a condition of the gastrointestinal tract based on the analysis of the one or more characteristics from the first time period relative to the second time period.

Any of the methods disclosed herein may include one or more of the following features or steps: the one or more characteristics include at least one of a frequency, an amplitude, a measure of roughness, a fractal dimension, a minimum, a maximum, a segment endpoint, a short-time Fourier transform, or a discrete time Fourier transform; the analyzing step may include calculating at least one of a short-time Fourier transform or a discrete time Fourier transform and evaluating the at least one of the short-time Fourier transform or the discrete time Fourier transform for indication of a shifting frequency of the electrical signal; the characterizing step may include classifying the electrical signal as indicative of an occurrence or imminence of an obstruction or a partial obstruction if the change is to a lower frequency, or as indicative of a cluster event or an imminent cluster event if the change is to a higher frequency; the method may include at least one of generating an alert or administering a treatment, based on the occurrence or the imminence of the condition of the gastrointestinal tract; or the electrical signal may be generated by at least one sensor located within the patient's body.

In another example, a system for evaluating gastrointestinal motility may include: a sensor configured to measure electrical activity of the gastrointestinal tract of a patient's body; and a processor configured to: receive an electrical signal that includes data pertaining to motility in the gastrointestinal tract; and analyze one or more characteristics of the electrical signal relative to one or more respective thresholds indicative of an occurrence or an imminence of a condition of the gastrointestinal tract.

Any of the systems disclosed herein may include one or more of the following features: the processor may be configured to, in the analyze step: compare a fractal dimension of the electrical signal to a first threshold value, if the fractal dimension is below the first threshold value, compare an amplitude of the electrical signal to a second threshold value, and evaluate whether an obstruction or a partial obstruction is occurring or imminent if the amplitude of the electrical signal is below the second threshold value; the processor may be configured to calculate one or more of a short-time Fourier transform or a discrete time Fourier transform of the electrical signal, analyze the one or more of the short-time Fourier transform or the discrete time Fourier transform for a change in frequency of the electrical signal, and classify the electrical signal as indicative of an occurrence or imminence of an obstruction or a partial obstruction if the change is to a lower frequency, or as indicative of a cluster event or an imminent cluster event if the change is to a higher frequency; the one or more characteristics of the electrical signal may include at least one of a frequency, an amplitude, a measure of roughness, a fractal dimension, a minimum, a maximum, a segment endpoint, a short-time Fourier transform, or a discrete time Fourier transform; the processor may be configured to, in the analyze step: compare a fractal dimension of the electrical signal to a first threshold value and, if the fractal dimension is below the first threshold value, compare an amplitude of the electrical signal to a second threshold value; the processor may be configured to, in the analyze step, evaluate whether an obstruction or a partial obstruction is occurring or imminent if the amplitude of the electrical signal is below the second threshold value; the processor may be configured to: calculate one or more of a short-time Fourier transform or a discrete time Fourier transform of the electrical signal and analyze the one or more of the short-time Fourier transform or the discrete time Fourier transform for a change in frequency of the electrical signal; the processor may be configured to classify the electrical signal as indicative of an occurrence or imminence of an obstruction if the change is to a lower frequency, or as indicative of a cluster event or an imminent cluster event if the change is to a higher frequency; the processor may be configured to, in the analyzing step, classify the electrical signal as indicative of a resting period or a fasting period if a fractal dimension of the electrical signal is lower than a threshold value; the processor may be further configured to characterize the electrical signal as pertaining to a particular portion of the gastrointestinal tract; the condition of the gastrointestinal tract may be at least one of an obstruction, a partial obstruction, a flare-up of an inflammatory bowel disease, a resting period, a fasting period, or a cluster event; the processor may be further configured to analyze trends in the one or more characteristics of the electrical signal; the electrical signal may be generated by at least one sensor located within the patient's body; a device configured to receive information from the sensor, wherein the sensor is in wireless communication with the device; a mechanism configured to administer one or more treatments; the processor may be configured to instruct the mechanism configured to administer one or more treatments to administer a treatment related to the occurrence or the imminence of a condition of the gastrointestinal tract; or the processor may be further configured to generate an alert indicative of the occurrence or the imminence of a condition of the gastrointestinal tract.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

The present disclosure is drawn to devices, systems, and methods for monitoring GI motility. In particular, in at least some aspects, the systems and methods may be used to monitor and/or predict IBD conditions, including flare-ups, by analyzing motility dysfunction. The motility monitoring devices, systems, and methods described herein, however, can be used to monitor other condition including, for example, other gastrointestinal conditions such as irritable bowel syndrome ("IBS"), cyclic vomiting syndrome ("CVS"), fecal incontinence ("FI"), chronic intestinal pseudo-obstruction ("CIP", which may also be known as Ogilvie Syndrome), and/or constipation. Although IBD monitoring is referenced herein, reference to IBD should not be construed as limiting the possible applications of the motility monitor.

Figure 1:
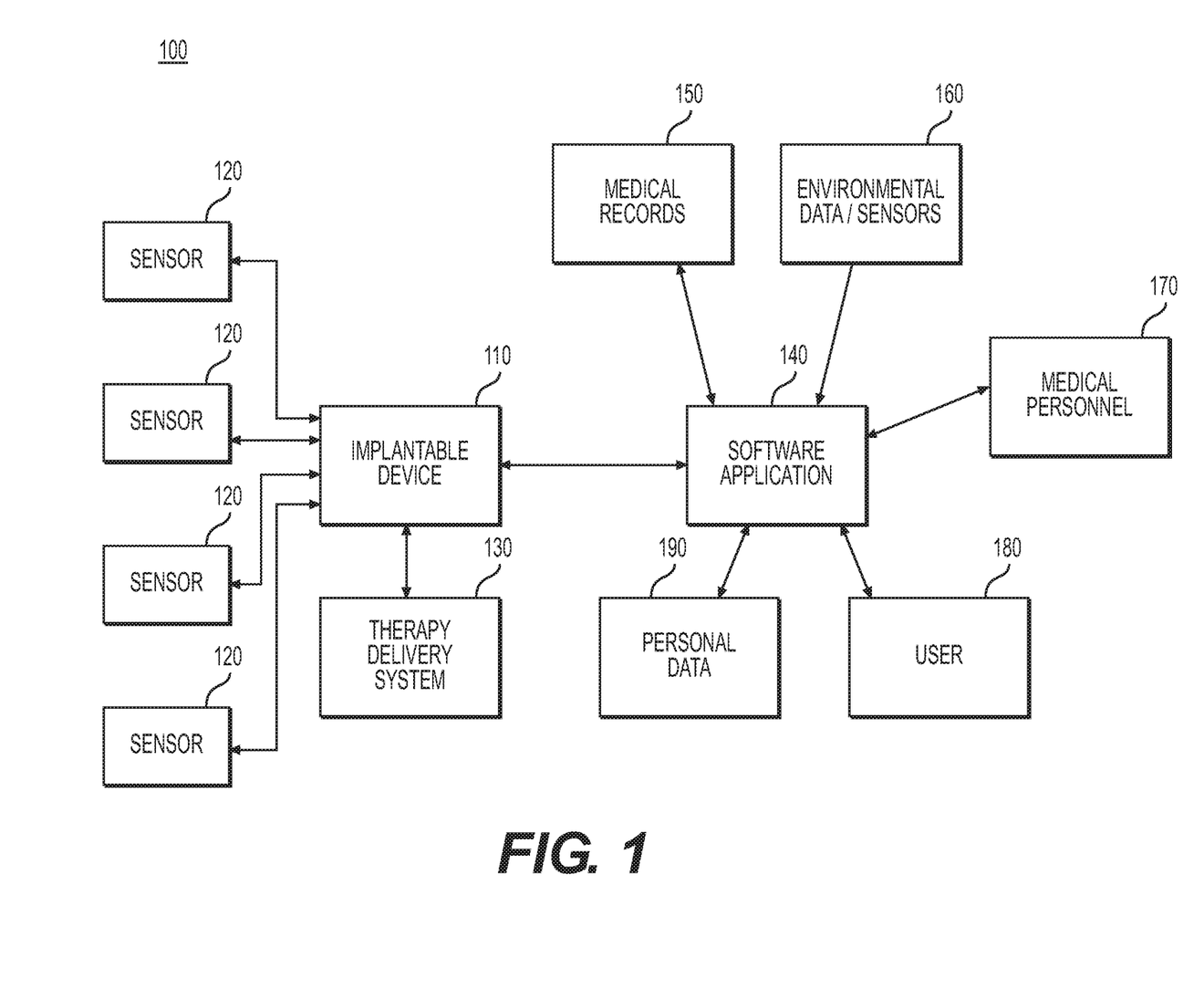
FIG. 1 depicts a block diagram of a system for monitoring GI motility.

FIG. 1 depicts a motility monitoring system 100. Motility monitoring system 100 may include one or more sensors 120, implantable device 110, therapy delivery system 130, software application 140, medical records input 150, environmental data input/sensors 160, medical personnel input 170, user input 180, and personal data input 190. Sensors 120 may directly or indirectly measure symptoms or physiological signals indicative of a flare-up or other state of IBD. Sensors 120 may be implanted in different regions of the GI tract or other parts of the body. For examples, sensors 120 may be implanted so as to measure activity of the stomach, duodenum, small intestine, and/or colon, including the parameters discussed below. Sensors 120 may also be outside of the body (i.e., not implanted). One or more sensors 120 may be associated with an implantable device 110. Implantable device 110 may be separate from one or more sensors 120 or may be combined with one or more sensors 120 in the same device. Sensors 120 may be one or more implants with one or more lead extensions in proximity to the gastric tract. The leads of sensors 120 may be proximate to, for example, the stomach, duodenum, small intestine, and/or colon.

Sensors 120 may be delivered via a natural orifice transluminal endoscopic surgery (NOTES) procedure, potentially during a colonoscopy. For example, during a colonoscopy, an incision may be made and a sensor may be implanted outside of the lumen on the omentum. Use of such a procedure may provide benefits including use of an endoscopy suite rather than an operating room. If sensors 120 require a battery, a battery may be changed during a routine colonoscopy. Sensors 120 may also be delivered via laproscopic surgery or a different surgical or non-surgical procedure.

Implantable device 110 and/or sensors 120 may be in communication with a software application 140. In the alternative, implantable device 110 and/or sensors 120 may be in communication with another type of processing unit. Software application 140 may run on a specialized device, a general-use smart phone or other portable device, and/or a personal computer. Software application 140 may also be part of implantable device 110 and may be wirelessly connected to medical records input 150, environmental data input/sensors 160, medical personnel input 170, user input 180, and personal data input 190. Software application 140 may be able to run on multiple platforms using data for the same patient. Multiple users may be able to access software application 140 concurrently or otherwise. Software application 140 or any other kind of processing unit may analyze signals from sensors 120 and extract information from the data obtained by sensors 120. In the alternative, implantable device 110 may analyze signals from sensors 120 and extract information from the data obtained by sensors 120. Software application 140 or any other suitable component may apply an algorithm to the signals or data from the sensors 120. The data from sensors 120 may be stored by software application 140 locally on a specialized device or a general-use device such as a smart phone or computer. In the alternative, the data from sensors 120 may be stored remotely by software application 140, for example in a cloud-based computing system.

Software application 140 may interface with a source of medical records 150. Software application 140 may further communicate with a source of environmental data 160. Environmental data source 160 may include environmental data sensors. Software application 140 may facilitate the entry of data by a user via user input 180 or by medical personnel via medical personnel input 170. Data may be entered via user input 180 and medical personnel input 170 either locally or remotely. User input 180 and medical personnel input 170 may constitute the same or separate components of motility monitoring system 100. Software application 140 may also communicate with personal data source 190. Medical records source 150, environmental data source 160, medical personnel input 170, user input 180, and personal data source 190 may be separate or may be integrated with one another in various combinations.

Motility monitoring system 100 may also include a therapy delivery system 130. Therapy delivery system 130 may be in communication with implantable device 110. In the alternative, therapy delivery system 130 may be in direct communication with software application 140. Therapy delivery system 130 may comprise the same physical component as implantable device 110 or may comprise a separate physical component. Therapy delivery system 130 may be used to administer drugs. Therapy delivery system 130 may also be used to administer other therapies such as neuromodulation therapy to, for example, block or stimulate nerves or other tissue, including via vagus nerve stimulation, peripheral nerve stimulation, sympathetic nerve modulation, gastric stimulation, or other tissue modulation therapies. Therapy delivery system 130 may form part of a closed loop system and may deliver therapy automatically based upon data from sensors 120 without user input. In the alternative, therapy delivery system 130 may be utilized manually by a user and/or medical personnel.

Sensors 120 can measure a wide variety of parameters regarding activity of the stomach, duodenum, small intestine, and/or colon. Depending on the parameter measured, different types of sensors 120 may be used. For example, gastric myoelectrical activity may be measured via, for example, electrogastrography ("EGG"). Gastric motility and/or dysmotility may be measured, via, for example, accelerometers, gyroscopes, pressure sensors, impedance gastric motility (IGM) using bioimpedance, strain gauges, optical sensors, acoustical sensors/microphones, manometry, and percussive gastogram. Gut pressure and/or sounds may be measured using, for example, accelerometers and acoustic sensors/microphones. Respiration rate may be measured using, for example, accelerometers, gyroscopes, and/or transthoracic impedance. Respiration rate so that software application 140 or another component can filter out respiratory activity from the GI signals software application 140 is analyzing. Certain of sensors 120 may be used only at certain times in order to conserve battery. For example, it may be desirable to perform a higher-frequency sampling with an EGG-type sensor 120 during rest or sleep to avoid external noise and obtain a cleaner signal.

Sensors 120 may also measure other factors which may have a correlation with flare ups and may indicate quality of life. For example, accelerometers, gyroscopes, GPS sensors, temperature sensors, blood pressure sensors, and the like may be used to measure factors such as posture; activity level; and sleep/waking cycles, including the depth, duration, and number of awakenings during sleep periods. Stress levels may be measured via heart rate sensors, galvanic skin response, respiratory sinus arrhythmia (using, for examples, sensors described above for respiration), or other autonomic tone measures. Stress levels may also be entered via manual input, for example via medical personnel input 170 or user input 180.

Gastric dysrhythmia may be measured with the types of measurements described above for gastric myoelectrical activity and gastric motility/dysmotility. Sensors 120 may also measure electro-mechanical uncoupling, which is where electrical activity is present but contractile activity is lacking. Sensors 120 may include acoustic, pressure, and/or other types of sensors to identify the presence of high electrical activity but low muscle response indicative of electro-mechanical uncoupling. When electro-mechanical uncoupling occurs, sensors 120, alone or in combination with the other components of motility monitoring system 100, may measure propagation of slow waves in regions such as the stomach, intestine, and colon. Software application 140 or another component of motility monitoring system 100 may classify any dysrhythmia as bradygastria (decreased activity), tachygastria (increased activity), or arrhythmia (irregular activity) for each region, such as the stomach, intestine, and/or colon.

Sensors 120, medical records source 150, environmental data source 160, medical personnel input 170, user input 180, and/or personal data source 190 may be used to record information in software application 140 regarding pain or discomfort levels; time of day/week/month/year; dietary intake; and environmental factors such as light, temperature, and altitude. Sensors 120, medical records source 150, environmental data source 160, medical personnel input 170, user input 180, and/or personal data source 190 may also be used to input demographic or other external data into software application 140. Such external data may include medical data such as prior relapse or flare-up information, medication (e.g., NSAIDs, antibiotics, hormone replacement therapy, oral contraceptives, cyclooxygenase-2, prednisone), surgeries (e.g. appendectomy or colectomy), comorbidities, and mental health information. Relevant external data may also include test data such as: gut microbiota, genomics, serological antibody markers, serological inflammatory markers (C-reactive protein, erythrocyte sedimentation rate (ESR), Interleukin (IL)-1Beta, IL-2, IL-6, IL-8, IL-10, IL-16, IL-2 soluble receptor, tumor necrosis factor-alpha (TNF-alpha), TNF-alpha soluble receptor, IFN-gamma), white blood cell count, intestinal permeability, endoscopy results (mucosal healing, confocal laser endomicroscopy, magnifying colonoscopy, etc.), histology results, and fecal markers (e.g., fecal calprotectin, lactoferrin, S100A12, Indium 111-labeled leukocytes, alpha1-antitrypsin, alpha2-macroglobulin, myeloperoxidase, PMNelastase). Relevant external data may further include personal data such as socioeconomic status, major life events, social media feeds, and internet searches.

Based on the data and information from sensors 120, medical records source 150, environmental data source 160, medical personnel input 170, user input 180, and/or personal data source 190, software application 140 may perform numerous analyses and generate various plots or other data. By way of example, software application 140 may analyze EGG data to determine, for example, morphology, including the dominant frequency and power (in each region); a power ratio or relative EGG power change; a percentage of normal slow waves; a percentage or other measurement of gastric dysrhythmia; and a percentage of EGG power distribution. Software application 140 may also, for example, analyze and/or plot circadian rhythms by analyzing, among other things, whether motility is increased at certain times (e.g., during daylight, after awakening, or after eating) and by generating a "normal," baseline trend for comparison purposes. Furthermore, software application 140 may perform time and frequency domain analysis of various signals to determine, for example, the maximum and minimum amplitude of signals, the frequency of signals, and the number of peak recordings in a signal.

Software application 140 may generate a notification if analysis of data from sensors 120 signals an upcoming disease flare-up or a flare-up in progress. Software application 140 may consider information from medical records source 150, environmental data source 160, medical personnel input 170, user input 180, and personal data source 190 when determining whether to deliver a notification. A predictive notification may be potentially generated by software application 140 up to days in advance of a flare-up. Notifications generated by software application 140 may be provided to a patient, a caregiver, and/or medical personnel. Information gathered by the software application 140 may be used to classify patients based on risk of flare-up in order to aid with predictive abilities. Software application 140 may also communicate with therapy delivery system 130 and may deliver therapy automatically based upon analysis of data from sensors 120 without user input. In the alternative, therapy delivery system 130 may be utilized manually by a user and/or medical personnel, e.g., after receiving an alert.

Figure 2:
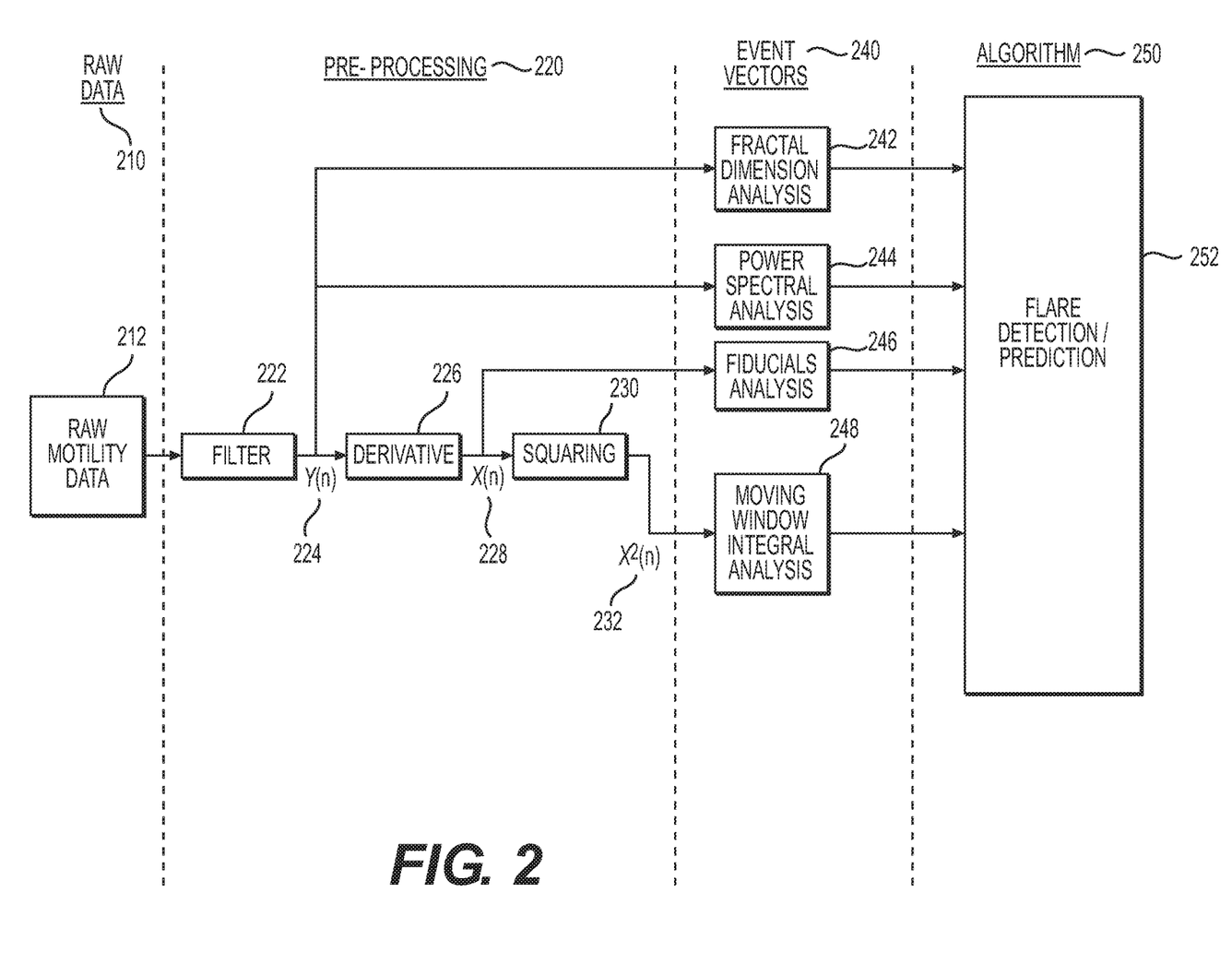
FIG. 2 depicts a flow chart showing methods for monitoring and/or predicting GI motility.
Figure 3A:
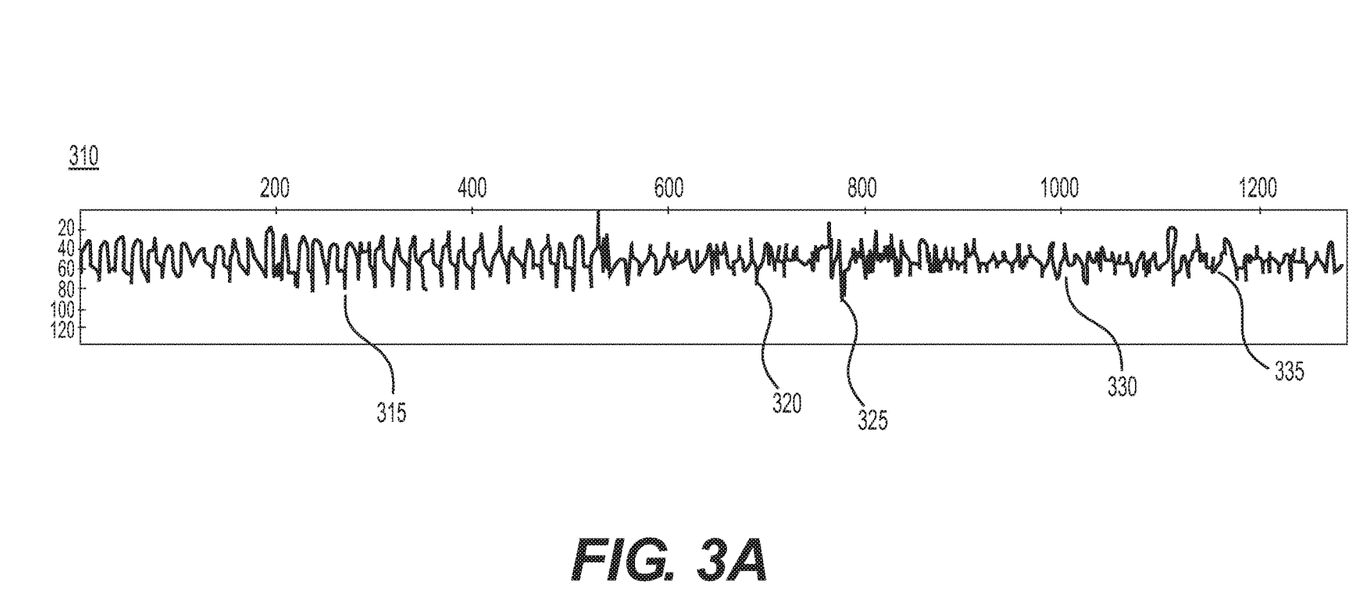
FIGS. 3A and 3B depict exemplary GI motility data.
Figure 3B:
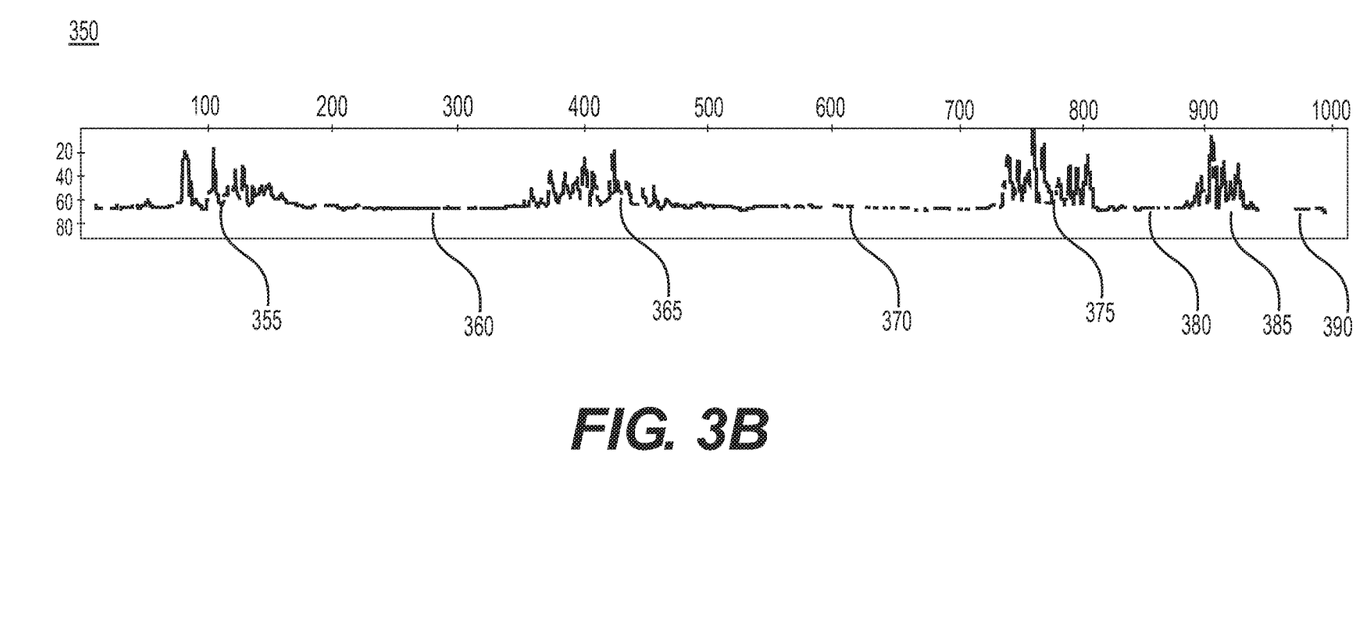
Figure 4:
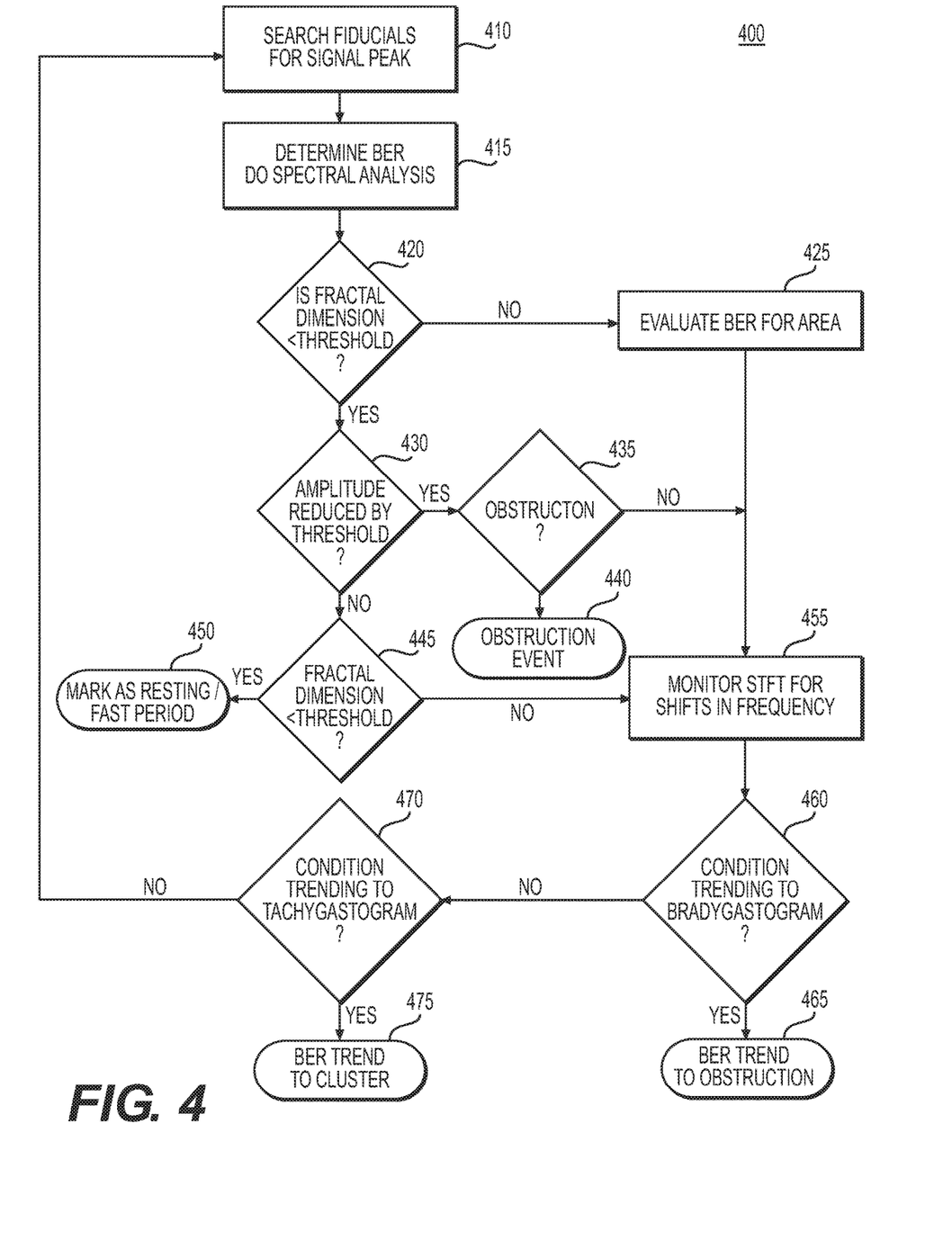
FIG. 4 depicts a flow chart showing methods for monitoring and/or predicting GI motility, according to one aspect of the disclosure.

As shown in FIGS. 2-4, a system such as motility monitoring system 100 as depicted in FIG. 1 may apply a variety of algorithms to data collected from implantable device 110, sensors 120, medical records source 150, environmental data source 160, medical personnel input 170, user input 180, and/or personal data source 190. In particular, software application 140 may apply the algorithms. The algorithms may be aided by machine learning. While motility monitoring system 100 is used as an exemplary system, it will be appreciated that the processes depicted in FIGS. 2-4 may be applied to data from other systems.

FIG. 2 shows a flow chart of an exemplary process for analyzing data, according to one aspect of this disclosure. The first stage is the raw data stage 210. Thereafter, pre-processing stage 220 may condition raw motility data 212 from raw data stage 210. Following pre-processing stage 220, event vectors stage 240 may generate relevant parameters. At algorithm stage 250, outputs of event vectors stage 240 may be analyzed. It should be noted that the steps of the pre-processing stage 220, event vectors stage 240, and algorithm stage 250 do not necessarily happen chronologically. For example, certain steps of event vectors stage 240 may take place concurrently with certain steps of pre-processing stage 220 or algorithm stage 250.

In raw data stage 210, raw motility data 212 is obtained from, for example, sensors 120 as depicted in FIG. 1. Raw motility data 212 may include data from one of sensors 120 or may be the compiled data from multiple sensors 120. For example, implantable device 110 and/or software application 140 may compile or otherwise process data from multiple sensors 120 in order to form raw data 212. Sensors 120 may communicate wirelessly with implantable device 110 and/or software application 140. If implantable device 110 compiles or otherwise processes raw motility data 212, raw motility data 212 may be communicated to software application 140 wirelessly. Sensors 120 may collect data continuously or at constant or variable time intervals. For example, time intervals may vary based on measurements from sensors 120 or other data such as time of day or patterns of disease activity. The measurements from sensors 120 may be compiled or otherwise processed into raw motility data 212 by implantable device 110 and/or software application 140 with the same frequency as the sensors 120 compile data. In the alternative, the measurements from sensors 120 may be compiled or otherwise processed into raw motility data 212 by implantable device 110 and/or software application 140 with a lower frequency than the sensors 120 compile data. For example, raw motility data 212 may be compiled or otherwise processed at constant time intervals or variable time intervals based on, for example, time of day or patterns of disease activity. Raw data 212 may be time-sampled data.

Raw motility data 212 may then enter pre-processing stage 220. The initial step of pre-processing stage 220 may be application of a filter in step 222. A bandpass filter may be utilized in filtering step 222. Gut motility signals generally fall in the range 0.05 Hz-0.25 Hz (3-15 cycles per minute ("cpm")). Therefore, a low-pass filter of a bandpass filter in filtering step 222 may be set at 1 Hz. A 1 Hz value may allow for evaluation of higher frequency clustered propagation events. A high-pass filter of a bandpass filter in filtering step 222 may be set at 0.05 Hz, the typical low end of the gut motility signal range. In the alternative, a high-pass filter may be set to pass signals with frequency greater than 0.083 Hz to avoid potential technical difficulties in using a filter with a lower pass frequency. A frequency of 0.083 Hz would allow for at least 5 cpm with some attenuation. In the alternative, only one of a high-pass filter or a low-pass filter may be used at filtering step 222. Following filtering step 222, output 224 (Y(n)) may be a filtered version of raw motility data 212. Output 224 may go on for further pre-processing and may also feed into fractal dimension analysis step 242 and power spectral analysis step 244 of event vectors stage 240, to be described further below.

Derivative step 226 may follow filtering step 222 in pre-processing stage 220. In derivative step 226, the output signal 224 of filtering step 222 may be differentiated. Derivative step 226 provides information about the slope of the incoming waveform. Discrete time derivatives may be used in derivative step 226 in order to obtain indications of peak detection of an incoming waveform because a peak may exist where the derivative changes from positive to negative. In contrast, a valley may exist where the derivative calculated in derivative step 226 changes from negative to positive. The output 228 (X(n)) of derivative step 226 may undergo further processing in squaring step 230 and may also be fed into a fiducials analysis step 246 of event vectors stage 240, to be described further below.

Squaring step 230 may follow derivative step 226 in pre-processing stage 220. In squaring step 230, output 228 may be squared or subject to another nonlinear operation which makes all data points positive and amplifies nonlinearly. Squaring step 230 emphasizes higher frequencies, which are mainly due to gastro-electrical activity. Output 232 (X2(n)) of squaring step 230 may be input into moving window integral analysis step 248 of event vectors stage 240. Output 232 may be hard limited to a certain maximum level corresponding to the number of bits used to represent the data type.

Event vectors stage 240 creates vectors or other outputs from data produced by various steps of pre-processing stage 220 or event vectors stage 240. For example, fractal dimension analysis step 242 may be performed on output 224 of filtering step 222. Fractal dimensioning is a mathematical technique. A box counting fractal dimension (BCFD) algorithm can be used to evaluate a waveform of varying amplitudes and frequencies. Fractal dimension describes the "roughness" of a line segment and is thus well-suited to physiological signals. Physiological waveforms like EGG outputs may be complex and therefore more difficult to represent mathematically, but the signal may be somewhat rhythmic and conducive to fractal dimensioning. Fractal dimension analysis using, e.g., BCFD, over a timespan of approximately 30 minutes can indicate presence or absence of dysmotility, e.g., an obstruction or partial obstruction. Motility monitoring system 100 may include parameters for a fractal dimension which corresponds to a healthy person or to the specific patient during a period of IBD (or other condition) remission. For example, the fractal dimension of a signal from a healthy person or a person not experiencing a flare-up may be approximately 1.20+/−0.14. Turning to FIG. 3A, a signal 310 from a healthy person shows a normal amount of variation in the signal. For example, segments 315, 320, 325, 330, and 335 all show variations in amplitude of the signal. A fractal dimension below the healthy range of 1.20+/−0.14 may indicate an obstruction or partial obstruction. Turning to FIG. 3B, a signal 350 indicating an obstruction or partial obstruction shows segments 355, 365, 375, and 385 with more activity and variability and segments 360, 370, 380, and 390 with lower variability. A fractal dimension above the healthy range of 1.20+/−0.14 may require further analysis such as by collecting more samples or by adjusting the window of evaluation and/or may also indicate that the patient is engaged in repetitive movement. Noise generally falls into a fractal dimension below 1, typically approximately 0.4-0.8. Noise may be the result of, for example, non-GI tract organ activity. For example, noise may result from respiration. A fractal dimension below a certain value, for example 0.5, may indicate periods of resting and/or fast.

Turning back to FIG. 2, power spectral analysis step 244 may be performed on output 224 of filtering step 222. Power spectral analysis step 244 may use a discrete time Fourier transform. Such an operation can identify cluster events, which may involve gastric hypermobility and delayed stomach emptying with abnormal intestinal pressure causing uncoordinated contractions. The discrete time Fourier transform may also help establish which area of the GI system is having an event or if clustering/bursting events are detected involving gastric hypermobility and/or delayed stomach emptying with abnormal intestinal pressure causing uncoordinated contractions. For example, the typical frequency range of the stomach may be 0.05 Hz (3 cpm)-0.083 Hz (5 cpm). The frequency range of the small intestines may be 0.09 Hz (5.5 cpm)-0.2 Hz (12 cpm). The frequency range of the large intestines may be 0.2 Hz (12 cpm)-0.25 Hz (15 Hz). Clustering or bursts may be indicated by frequencies of approximately 0.33 Hz (20 cpm)-0.5 Hz (30 cpm). In addition or in the alternative, a short-time Fourier transform (STFT) may be utilized to further evaluate frequency shifting to evaluate any gastric rate variability trending to either bradygastric (slowing activity in the region) or tachygastric (increasing activity) when evaluated with longer term averages and histograms from the spectral analysis. Gastric rate variability may be indicative of an upcoming flare-up. For example, a trend toward bradygastria may be predictive of slowing of motility and a trend toward tachygastria may be predictive of an abnormal increase in motility.

Fiducials analysis step 246 may be performed on output 228 of derivative step 226. Through fiducials extraction in fiducials analysis step 246, waveform fiducials (e.g., min, max, cluster end points, rest end points) can be created.

Moving window integral analysis step 248 may be performed on output 232 of squaring step 230. The outputs of power spectral analysis step 244 may also be utilized in moving window integral analysis step 248. Moving window integral analysis step 248 may be used because slope alone may not detect a gastric electrical activity ("GEA") event.

Many GEAs may have abnormal complexes—e.g., GEAs may have large amplitudes and long durations but not steep slopes that would be detected using information about only slope of the peak basis electrical rhythm ("BER," which may also be referred to as "slow waves"). In moving window integral analysis step 248, the evaluation may dynamically adjust to a GEA depending on the sampling rate and number of samples. If outputs of power spectral analysis step 244 are utilized, frequency information from a power spectrum of a BER section may be used to set a window threshold according to the following equation:

moving window=1/(2(*BER(Hz)))

The outputs of one or more of the steps of event vectors stage 240 may be used by flare-up detection/prediction algorithm 252 in algorithm stage 250. Parameters output by event vectors stage 240, as discussed previously, may be used to evaluate, for example, signal peak vs. noise peak; baseline for BER and GEA over average samples; and whether fractal dimension D is leaning toward dysfunctional motility, to monitor fractal dimension, and to monitor STFT for any trends to brady- or tachy-gastric events. Algorithm 252 may thus evaluate whether a patient's current state, for example whether a patient is currently experiencing a flare-up or is in a resting/fast period. Algorithm 252 may also engage in predictive analysis to determine, for example, whether there is a trend toward an obstruction (or partial obstruction) event or a trend toward a cluster event FIG. 4 shows an example flare-up detection/prediction algorithm 400. While FIG. 4 shows exemplary steps, it will be understood by persons of ordinary skill in the art that certain steps may be omitted or additional steps may be added. And while FIG. 4 shows an exemplary ordering of steps, it will be understood by those of skill in the art that the steps of algorithm 400 may be performed in an alternative order or may be performed concurrently with one another. Some portions of the discussion below reference steps from FIG. 2. In addition to or in the alternative to the steps from FIG. 2, other processing steps may be utilized or raw data may not be processed before an algorithm is applied. Processing steps from FIG. 2 or other processing steps may be conducted prior to application of algorithm 400 or concurrently with application of algorithm 400. In other words, certain processing steps from FIG. 2 or other processing steps may be performed concurrently with or between steps of algorithm 400. The threshold values discussed below are exemplary, and other values may be used. For example, thresholds may be universal across patients, vary across patient class, or vary across particular patients. Thresholds may or may not be static and may change over time. Thresholds may be generated automatically by a portion of motility monitor 100 as depicted in FIG. 1, for example software application 140. For example, thresholds may be generated by machine learning or another mechanism. In the alternative, a relevant threshold may be input via medical personnel input 170 or user input 180 or any other relevant input, either locally or remotely. Other aspects of algorithm 400 may be modified via, for example, a portion of motility monitor 100, as described above for the threshold values.

In step 410, fiducials may be searched for signal peaks. For example, signal peaks may be determined using the results of fiducials analysis step 246, as described with regard to FIG. 2. Signal peaks may be determined in order to determine, for example, the frequency of the signal, since each cycle has one peak. As part of step 410, signal peaks may be evaluated to determine if a signal under inspection is an actual signal peak or a noise peak. For example, a signal may have a local maximum which is smaller than a typical signal peak. Such a local maximum may be indicative of noise rather than a signal. Various techniques which are known or may become known may be used to distinguish between signal and noise. Signal peaks may be differentiated from noise peaks in order to focus analysis on relevant GI activity rather than noise signals that could result from, for example, respiration or activity of other organs outside of the GI tract. For example, if respiration rate has been analyzed for a patient, the information obtained may be used to separate the primary signal from noise. In the alternative to determining peaks, other parameter(s) may be used for determining characteristics of the signals. For examples, valleys of a signal or another characteristic may be determined.

In step 415, the BER or other signal may be further characterized by other parameters. While a BER is referred to below, any other relevant signal may be analyzed. For example, spectral analysis may be used and the BER of the GEA waveform may be determined because the BER represents the contractions of the GI tract. For example, the result of power spectral analysis 244 as described with regard to FIG. 2 may be used in step 415. The result of moving window integral analysis step 248 may also be utilized in step 415. In addition, an average BER frequency may be calculated for a given portion of the GI tract in order to develop a baseline value. Such a baseline value may be compared to measurements taken at a given time in order to determine whether a given BER has a greater or lesser frequency than the baseline. Baseline frequencies may be determined for different regions of the GI tract, for example the stomach, the small intestine, and the large intestine. A baseline may also be developed for other characteristics such as amplitude or slope of a BER signal.

In step 420, the fractal dimension or other relevant parameter may be analyzed in order to further evaluate whether a signal is indicative of a flare-up or other condition. For example, fractal dimension may be analyzed as described in step 242, described with regard to FIG. 2. As discussed above, a fractal dimension may be indicative of whether a flare-up is currently occurring or will occur in a relevant future time frame (for example, within the next few days). If the fractal dimension is less than a threshold which may be generalized across patients or specific to a particular patient or class of patients, there may be dysmotility or a trend toward dysmotility. For example, the relevant threshold may be 1.04 or another value. If the fractal analysis is greater than the relevant threshold (for example, 1.04), then the signal is more persistent. In the alternative, a parameter other than fractal dimension may be used to evaluate whether a flare-up is occurring or imminent. In any case, further analysis as described above may be necessary to determine whether a flare-up is occurring or will occur in a relevant future time frame.

If the fractal dimension analyzed in step 420 is less than the threshold, then the amplitude of the signal may be analyzed in step 430 because a signal which has a reduced amplitude may be indicative of an obstruction or partial obstruction event. A specific threshold may be used for determining a relevant decrease in amplitude. In the alternative, another parameter or value may be used.

If the amplitude of the signal has not been reduced by a particular threshold, for example 20%, in step 430, then, in step 445, the fractal dimension may be analyzed to determine if it is less than a threshold indicative of a resting and/or fast period. For example, the threshold may be 0.5. The threshold value used may vary. For example, a different value can be used for all patients, or a value may be determined based on a class of patients or on a specific patient. In the alternative, another parameter can be used in step 445 to classify whether a patient is experiencing a fasting and/or resting period.

If the fractal dimension analyzed in step 445 is lower than the threshold (for example 0.5), or step 445 otherwise indicates a fasting and/or resting period, then the event is marked as a resting/fasting period in step 450. If an event is marked as a resting/fasting period in step 450, further analysis may not be required. The steps of algorithm 400 may be performed again after a set time period or after a time period based on previous patterns of a given patient or set of patients. The steps of algorithm 400 may, for example, be performed less frequently during periods which have been marked as resting/fast periods. Additionally or alternatively, the steps of algorithm 400 may be performed more or less frequently based on time of day or other external factors.

If the fractal dimension analyzed in step 445 is not less than the relevant threshold (for example, 0.5) or the analysis of step 445 otherwise indicates against a fasting and/or resting period, then further analysis may be necessary. For example, a signal may be analyzed for shifts in frequency. For example, an STFT transform or other parameter may be measured for shifts in frequency in step 455, as described further below. In the alternative, or in addition, following step 435, the BER or other signal may be analyzed for the relevant area, as described in step 425 and as described further below. If step 425 is performed following step 435, then step 455 may follow step 425.

If, in step 430, the amplitude has been reduced by the relevant threshold (for example 20%), in step 435 it is determined whether there is an obstruction or a partial obstruction. For example, it may be verified that the fractal dimension is below the relevant threshold and the amplitude has been reduced by the relevant threshold. For example, the fractal dimension and/or amplitude may be analyzed again. If there is an obstruction or a partial obstruction, then the signal is classified as an obstruction event in step 440. Further analysis steps may not be necessary after a signal is classified as an obstruction event in step 440. The steps of algorithm 400 may be repeated as discussed above. For example, steps of algorithm 400 may be performed more often after an obstruction event is classified in step 440 in order to determine the end point of an obstruction event. As discussed in further detail below, when a signal is classified as a particular type of event (for example as an obstruction event in step 440), an alarm may sound, a user and/or medical professional may be alerted, and/or therapy may be initiated. For example, a component of motility monitoring system 100 as described with regard to FIG. 1 may provide an alarm, notification, and/or therapy.

If it is determined that there is not an obstruction in step 435, then a signal may be analyzed for shifts in frequency. For example, an STFT transform or other parameter may be measured for shifts in frequency in step 455, as described further below. In the alternative, or in addition, following step 435, the BER or other signal may be analyzed for the relevant area, as described in step 425 and as described further below. If step 425 is performed following step 435, then step 455 may follow step 425.

If a fractal dimension is not less than the threshold, or the fractal dimension or other relevant parameter is not indicative of obstruction or partial obstruction in step 420, then in step 425 the BER or other signal may be evaluated to determine the area of origin. For example, frequency may be used. By way of example, the frequency of the BER or other signal may be determined in step 425 or may have been determined in steps 410 or 415, discussed above. For example, the stomach may have a BER frequency of 3-5 cpm, the small intestines may have a BER frequency of 5.5-12 cpm, and the large intestine may have a BER frequency of 12-15 cpm. In the alternative, the data such as raw data 212 as described with regard to FIG. 2, may carry information about the location of a sensor 120 as described with regard to FIG. 1. If sensor location information is utilized, step 425 may be omitted or may be used to confirm location information. Area of origin may be analyzed because different baseline BER frequencies may be relevant for different regions. What magnitude of shift in BER from baseline is indicative of a flare-up may also vary depending on the area of origin.

In step 455, analysis may be conducted of frequency shifts. For example, power spectral analysis step 244 may be used. As explained above, STFT may be used as part of power spectral analysis step 244. In the alternative, a different method of analyzing frequency shift may be used. For example, as discussed above with regard to step 244, a discrete time Fourier transform may be used. While the below discussion references STFT, references to STFT shall be understood to refer to any relevant method of measuring frequency shifts. Frequency shifts may be predictive of flare-ups of IBD or other conditions.

Following step 455, if an STFT indicates that the condition is trending to bradygastogram in step 460, then the BER may be classified as having a trend toward obstruction or partial obstruction in step 465. Bradygastria is associated with obstruction, so shifts in frequency toward bradygastria may be predictive of obstruction, even if bradygastria has not yet occurred. In other words, even before bradygastria occurs, analysis may show that frequency is moving toward bradygastria and thus obstruction may occur. Following step 465, further analysis may not be required, and algorithm 400 may be repeated as discussed above. For example, algorithm 400 may be repeated more frequently when a trend toward obstruction or partial obstruction is identified in step 465.

If the STFT does not indicate a trend toward bradygastogram in step 460, then the STFT is analyzed to determine whether the condition is trending toward tachygastogram in step 470. If the condition is trending to tachygastrom in step 470, the BER is classified as having a trend toward cluster in step 475. Tachygastria is associated with cluster events, so shifts in frequency toward tachygastria may be predictive of cluster, even if tachygastria has not yet occurred. In other words, even before tachygastria occurs, analysis may show that frequency is moving toward tachygstria and thus cluster may occur. Following step 470, further analysis may not be required, and algorithm 400 may be repeated as discussed above. For example, algorithm 400 may be repeated more frequently when a trend toward cluster is identified in step 470. As discussed in further detail below, when a signal is classified as a particular type of event (for example as cluster event in step 440), an alarm may sound, a user and/or medical professional may be alerted, and/or therapy may be initiated. For example, a component of motility monitoring system 100 as described with regard to FIG. 1 may provide an alarm, notification, and/or therapy.

If, in step 470, the STFT does not indicate a condition trending to tachygastogram, then the process may begin again at step 410 and the fiducials are searched for signal peaks. This repetition may occur immediately or with some delay following step 470.

While the above discussion referred to bradygastria and tachygastria, it will be understood that algorithm 400 can be used to monitor changes in frequency or other parameters of a variety of signals present in the body in order to analyze whether the signal indicates a condition of concern.

Depending on the outcome of algorithm 400 (for example, an obstruction or partial obstruction event in step 440, a trend toward obstruction or partial obstruction in step 465, or a trend toward cluster in step 475), a system such as motility monitoring system 100 may take action such as alerting a user or a medical professional, as indicated above. Such an alert may take the form of, for example, an alarm. Software application 140 may consider information from medical records source 150, environmental data source 160, medical personnel input 170, user input 180, and personal data source 190 when determining whether to deliver a notification. Motility monitoring system 100 may alternatively take any other pertinent action as a result of algorithm 400. For example, motility monitoring system 100 may dispense therapy via therapy delivery system 130. Motility monitoring system 100 may also update medical records via medical records 150. The actions taken in response to an event (for example, an obstruction or partial obstruction event in step 440, a trend toward obstruction or partial obstruction in step 465, or a trend toward cluster in step 475) may vary depending on numerous factors including, for example, severity, type of event, event timing, historical data, patient preferences, and/or medical professional preferences.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A method for evaluating a gastrointestinal tract, the method comprising:
   receiving an electrical signal obtained by a sensor via at least one lead extension of the sensor positioned proximate to the gastrointestinal tract, the electrical signal including data pertaining to motility in the gastrointestinal tract of a patient;
   analyzing a first set of one or more of a plurality of characteristics of the electrical signal relative to a first threshold value indicative of an imminence of a condition of the gastrointestinal tract within a predefined future time frame;
   in response to the analyzing of the first set indicating the imminence of the condition, analyzing a second set of one or more of the plurality of characteristics of the electrical signal relative to a second threshold value indicative of a type of the condition to determine the type of the condition, the second set of the one or more of the plurality of characteristics analyzed including a frequency of the electrical signal, to determine the type of the condition as trending toward one of bradygastria or tachygastria, based on measured shifts in the frequency and in response to no obstruction or resting period being determined; and
   administering a treatment based on the indicated imminence and the determined type of the condition, the treatment including one or more of neuromodulation or tissue modulation therapy specific to the determined type of the condition.

2. The method of claim 1, wherein the plurality of characteristics of the electrical signal include at least one of a frequency, an amplitude, a measure of roughness, a fractal dimension, a minimum, a maximum, a segment endpoint, a short-time Fourier transform, or a discrete time Fourier transform.

3. The method of claim 1, wherein the analyzing of the first set includes:
   comparing a fractal dimension of the electrical signal to the first threshold value, wherein the fractal dimension being below the first threshold value indicates the imminence of the condition.

4. The method of claim 1, wherein the analyzing of the second set includes:
   comparing a reduction in an amplitude of the electrical signal to the second threshold value;
   in response to determining that the amplitude has been reduced by at least the second threshold value, evaluating whether an obstruction or a partial obstruction is the type of the condition that is imminent; and
   in response to determining that the obstruction or the partial obstruction is not the type of the condition, analyzing the frequency of the electrical signal to determine the type of the condition as trending toward one of bradygastria or tachygastria based on the measured shifts in the frequency.

5. The method of claim 1, wherein analyzing the frequency of the electrical signal to determine the type of the condition further comprises:
   calculating one or more of a short-time Fourier transform or a discrete time Fourier transform of the electrical signal; and
   analyzing the one or more of the short-time Fourier transform or the discrete time Fourier transform for a change in frequency of the electrical signal.

6. The method of claim 5, further comprising:
   classifying the electrical signal as indicative of an occurrence or imminence of bradygastria that is associated with an obstruction or a partial obstruction if the change is to a lower frequency, or as indicative of tachygastria that is associated with a cluster event or an imminent cluster event if the change is to a higher frequency.

7. The method of claim 1, wherein the analyzing of the second set includes:
   comparing a reduction in an amplitude of the electrical signal to the second threshold value;
   in response to determining that the amplitude has not been reduced by at least the second threshold value, comparing a fractal dimension of the electrical signal to a third threshold value; and
   in response to the fractal dimension of the electrical signal being higher than the third threshold value, determining that a resting period is not occurring, and analyzing the frequency of the electrical signal to determine the type of the condition as trending toward one of bradygastria or tachygastria based on the measured shifts in the frequency.

8. The method of claim 1, wherein the type of the condition of the gastrointestinal tract includes at least one of an obstruction or a partial obstruction when the type of the condition is determined as trending toward bradygastria, or a cluster event when the type of the condition is determined as trending toward tachygastria.

9. The method of claim 1, further comprising analyzing trends in the plurality of characteristics of the electrical signal.

10. The method of claim 1, wherein sensor is located within the patient.

11. The method of claim 1, further comprising generating an alert based on the indicated imminence and the determined type of the condition of the gastrointestinal tract.

12. A method for evaluating a gastrointestinal tract, the method comprising:
receiving an electrical signal obtained by a sensor via at least one lead extension of the sensor positioned proximate to the gastrointestinal tract, the electrical signal including data pertaining to motility in the gastrointestinal tract of a patient;
analyzing one or more of a plurality of characteristics of the electrical signal relative to one or more respective thresholds to determine an occurrence or an imminence of a condition of the gastrointestinal tract and a type of the condition, wherein the analyzing includes:
determining that a fractal dimension of the electrical signal is below a first threshold value, wherein the fractal dimension being below the first threshold value indicates the occurrence or the imminence of the condition; and
in response to the determining that the fractal dimension is below the first threshold value, comparing a reduction in an amplitude of the electrical signal to a second threshold value indicative of the type of the condition to determine the type of the condition, wherein, when the amplitude has been reduced by at least the second threshold value, the type of the condition is determined as an obstruction event, and wherein, when the amplitude has not been reduced by at least the second threshold value, the type of the condition is determined as trending toward one of bradygastria or tachygastria further based on measured shifts in frequency; and
administering a treatment based on the indicated occurrence or imminence and the determined type of the condition, the treatment including one or more of neuromodulation or tissue modulation therapy specific to the determined type of the condition.

13. The method of claim 12, wherein, when the amplitude has not been reduced by at least the second threshold value, determining the type of condition as trending toward one of bradygastria or tachygastria further based on the measured shifts in the frequency comprises:
calculating one or more of a short-time Fourier transform or a discrete time Fourier transform of the electrical signal; and
analyzing the one or more of the short-time Fourier transform or the discrete time Fourier transform for a change in frequency of the electrical signal.

14. The method of claim 13, further comprising:
classifying the electrical signal as indicative of an occurrence or imminence of bradygastria that is associated with a trend toward an obstruction or a partial obstruction based on the change being to a lower frequency.

15. The method of claim 13, further comprising:
classifying the electrical signal as indicative of an occurrence or imminence of tachygastria that is associated with a trend toward a cluster event based on the change being to a higher frequency.

16. A method for evaluating a gastrointestinal tract, the method comprising:
receiving an electrical signal obtained by a sensor associated with an implantable device, the electrical signal including data pertaining to motility in the gastrointestinal tract of a patient;
determining an occurrence or an imminence of a condition of the gastrointestinal tract based on an analysis of a first set of one or more of a plurality of characteristics of the electrical signal relative to a first threshold;
determining a type of the condition as one of an obstruction event, bradygastria associated with a trend toward an obstruction event, or tachygastria associated with a trend toward a cluster event based on an analysis of a second set of one or more of the plurality of characteristics of the electrical signal relative to one or more additional thresholds different from the first threshold; and
administering a treatment based on one or more of the occurrence or the imminence of the condition of the gastrointestinal tract and the type of the condition, the treatment including one or more of neuromodulation or tissue modulation therapy specific to the type of the condition.

17. The method of claim 16, wherein the sensor and the implantable device comprise a single physical component.

18. The method of claim 16, wherein administering the treatment includes causing a therapy delivery system to automatically operate to administer the treatment, wherein the therapy delivery system, the sensor, and the implantable device comprise a single physical component.

19. The method of claim 18, wherein operating the therapy delivery system includes administration of one or more drugs as part of the one or more of neuromodulation or tissue modulation therapy.

20. The method of claim 1, further comprising:
filtering the electrical signal received to identify the data pertaining to motility, wherein the first set and the second set of the one or more of the plurality of characteristics analyzed are characteristics of the filtered electrical signal.

* * * * *